United States Patent
Edwin et al.

(10) Patent No.: US 6,203,735 B1
(45) Date of Patent: *Mar. 20, 2001

(54) METHOD OF MAKING EXPANDED POLYTETRAFLUOROETHYLENE PRODUCTS

(75) Inventors: Tarun J. Edwin, Tempe; Scott Randall, Mesa, both of AZ (US)

(73) Assignee: Impra, Inc., Tempe, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/792,780

(22) Filed: Feb. 3, 1997

(51) Int. Cl.[7] .................................................. B29C 69/02
(52) U.S. Cl. .................. 264/127; 264/210.2; 264/210.5; 264/294; 264/331.14
(58) Field of Search ................................ 264/127, 210.2, 264/210.1, 211.12, 294, 296, 331.14, 319, 210.5; 425/392

(56) References Cited

U.S. PATENT DOCUMENTS

| Re. 31,341 | 8/1983 | Koizumi et al. ..................... 526/73 |
| 3,196,194 | * 7/1965 | Ely, Jr. et al. . |
| 4,104,394 | * 8/1978 | Okita ..................................... 264/89 |
| 4,208,745 | * 6/1980 | Okita ................................. 264/288.8 |
| 4,234,535 | * 11/1980 | Okita ................................... 264/519 |
| 4,596,837 | 6/1986 | Yamamoto ........................... 521/145 |
| 4,647,416 | 3/1987 | Seiler, Jr. et al. .................. 264/118 |
| 4,655,769 | 4/1987 | Zachariades ............................. 623/1 |
| 4,671,754 | * 6/1987 | Okita et al. ........................... 264/127 |
| 4,714,748 | 12/1987 | Hoashi et al. ........................ 526/255 |

(List continued on next page.)

FOREIGN PATENT DOCUMENTS 0 648 869   4/1995   (EP) .

OTHER PUBLICATIONS

"The melting temperature of polytetrafluoroethylene" by Y.P. Khanna, *Journal of Materials Science Letters*, vol. 7, pp. 817–818 (1988).

"Glass Transition of Poly(tetrafluoroethylene)" Suk Fai Lau, J. Wesson and B. Wunderlich, *Macromolecules*, vol. 17, pp. 1102–1104 (1984).

"The Density of Amorphous Polytetrafluoroethylene" *Journal of Polymer Science: Polymer Physics Edition*, vol. 20, pp. 2159–2161 (1982).

"A New Differential Scanning Calorimetry Based Approach for the Estimation of Thermal Conductivity of Polymer Solids and Melts" by Y.P. Khanna, T.J. Taylor, and G. Chomyn, *Polymer Engineering and Science*, vol. 28, No. 16, pp. 1034–1041 (Aug. 1988).

(List continued on next page.)

*Primary Examiner*—Jan H. Silbaugh
*Assistant Examiner*—Mark Eashoo
(74) *Attorney, Agent, or Firm*—Morrison & Foerster LLP; Todd W. Wight (57) ABSTRACT

A method of shaping three-dimensional products by manipulating an expanded polytetrafluoroethylene tubular body into a desired three-dimensional conformation. The present invention entails radially expanding a longitudinally expanded polytetrafluoroethylene (ePTFE) tube to form a radially expanded ePTFE (rePTFE) tube, engaging the rePTFE tube circumferentially about a shaping mandrel, heating the assembly to a temperature below the crystalline melt point temperature, or sintering temperature, of polytetrafluoroethylene to radially shrink the diameter of the rePTFE tube into intimate contact with the shaping mandrel, and heating the assembly to a temperature above the crystalline melt point temperature of polytetrafluoroethylene to amorphously lock the microstructure of the shaped polytetrafluoroethylene body.

21 Claims, 6 Drawing Sheets

U.S. PATENT DOCUMENTS

| | | | |
|---|---|---|---|
| 4,760,102 | 7/1988 | Moriyama | 521/145 |
| 4,816,339 | 3/1989 | Tu et al. | 623/1 |
| 4,830,062 | 5/1989 | Yamamoto | 138/177 |
| 4,957,669 | 9/1990 | Primm | 264/23 |
| 5,061,276 | 10/1991 | Tu et al. | 623/1 |
| 5,071,609 | 12/1991 | Tu et al. | 264/119 |
| 5,084,065 | 1/1992 | Weldon et al. | 623/1 |
| 5,123,917 | 6/1992 | Lee | 623/1 |
| 5,143,122 * | 9/1992 | Adkins | 138/109 |
| 5,152,782 | 10/1992 | Kowligi et al. | 623/1 |
| 5,171,805 | 12/1992 | Tatemoto | 526/252 |
| 5,234,739 | 8/1993 | Tanaru et al. | 428/131 |
| 5,376,110 | 12/1994 | Tu et al. | 623/1 |
| 5,387,236 | 2/1995 | Noishiki | 623/1 |

OTHER PUBLICATIONS

"The Thermodynamic Properties of Polytetrafluoroethylene" by Suk Fai Lau, H. Suzuki, and B. Wunderlich, *Journal of Polymer Science: Polymer Physics Edition*, vol. 22, pp. 379–405 (1984).

"A Study on the Thermal Behaviour and Structural Characteristics of Polytetrafluroethylene" by V. Villani, *Thermochimica Acta*, vol. 162, pp. 189–193 (1990).

"Use of Stents Covered with Polytetrafluroethylene in Experimental Abdominal Aortic Aneurysm" by J. Palmaz, et al., *JVIR*, vol. 6, pp. 879–885 (1995).

"Characterization of the crystallinity of polytetrafluoroethylene by X–ray and IR spectroscopy, differential scanning calorimetry, viscoelastic spectroscopy and the use of a density gradient tube" by Ting–Yung Hu, Wear, vol. 82, pp. 369–376 (1982).

"X–ray analysis and differential scanning calorimetry for the study of crystallinity of poly(tetrafluoroethylene" by B.A. Briskman, V.N. Rogova, V. Dudarev, and A. Noifekh, *Vysokomol. Soedin., Ser. B*, vol. 31, No. 7, pp. 539–543 (1989).

* cited by examiner

METHOD OF MAKING EXPANDED POLYTETRAFLUOROETHYLENE PRODUCTS

REFERENCE TO RELATED APPLICATIONS

This application is related to co-pending, commonly assigned PCT International Application Serial No. PCT/US96/02715, filed Feb. 28, 1996, entitled "Apparatus and Method for Making Flanged End-to-Side Anastomosis."

BACKGROUND OF THE INVENTION

The present invention relates generally to methods of making shaped three-dimensional products from microporous expanded polytetrafluoroethylene. More particularly, the present invention relates to a method of shaping three-dimensional products by manipulating an expanded polytetrafluoroethylene tubular body into a desired three-dimensional conformation. The present invention entails radially expanding a longitudinally expanded polytetrafluoroethylene (ePTFE) tube to form a radially expanded ePTFE (rePTFE) tube, engaging the rePTFE tube circumferentially about a shaping mandrel, heating the assembly to a temperature below the crystalline melt point temperature, or sintering temperature, of polytetrafluoroethylene to radially shrink the diameter of the rePTFE tube into intimate contact with the shaping mandrel, and heating the assembly to a temperature above the crystalline melt point temperature of polytetrafluoroethylene to amorphously lock the microstructure of the shaped polytetrafluoroethylene body.

The three-dimensional shaped microporous expanded polytetrafluoroethylene products made in accordance with the method of the present invention are particularly well suited for use as medical implants, and are particularly useful as venous or arterial prostheses either as vein or artery replacements, as endovascular liners, arterio-venous shunts, or as venous access grafts. As arterial or venous prosthesis, shaped microporous expanded polytetrafluoroethylene grafts have been made which have a flanged cuff section contiguous with an elongate tubular section. The cuffed prosthesis are particularly well suited for use in end-to-side anastomoses such as that required in femoro-popliteal bypass procedures where the flanged cuff section is sutured about an open arteriotomy to form the end-to-side anastomosis. As endovascular liners, the shaped expanded polytetrafluoroethylene products may be configured to have a taper along its longitudinal axis, with a proximal end having either a larger or smaller inner diameter than the distal end, or may have a step taper, where there is a tapered transition zone between two different inner diameter sections, or the product may be configured to have an intermediate section of a larger diameter than proximal or distal ends of the product, or the product may be configured into a bifurcated or trifurcated graft where each of the legs is formed from appropriately sized appendage sections of a base tubular graft member.

BACKGROUND OF THE PRIOR ART

Conventional processes for making ePTFE products are typically limited to fabricating sheets, tubes, rods or filaments. Methods for making complex conformational shapes of ePTFE are unknown in the prior art. The prior art is limited in its teaching to methods of making heat shrinkable tubing of either fluoroethylene co-polymers (FEP) or of non-expanded polytetrafluoroethylene (nPTFE). However, the uses of FEP and nPTFE heat shrink tubes has been limited to tubular profiles. Conventional methodologies are represented, for example, by Ely, Jr., el aL U.S. Pat. No. 3,196,194 issued in 1965, which discloses a FEP-Fluorocarbon Heat Shrinkable Tubing which is first expanded 33 to 100 percent of the initial internal diameter and is then correspondingly heat shrinkable by a factor of 33 to 100 percent diameter at 250–400° F. This patent teaches that expansion of the FEP-Fluorocarbon tubing may be accomplished by introducing a positive gas pressure into the lumen of a closed-end tube of the FEP-fluorocarbon. Seiler, Jr. et al. U.S. Pat. No. 4,647,416 issued Mar. 3, 1987 discloses a polytetrafluoroethelyne (PTFE) tube and a method of making the tube by creating radial scores in the outer surface of unsintered PTFE tubing and either longitudinally stretching the tubing to separate the score lines into discrete ribs or subjecting the tubing to sintering temperatures to cause shrinkage of the PTFE intermediate the score lines to differentiate the score lines into ribs during the sintering process.

Tu, et al. disclosed a trilogy of references which disclose methods of fabricating ePTFE elastomer impregnated materials which are radially and/or longitudinally compliant. U.S. Pat. No. 4,816,339 issued Mar. 28, 1989 discloses a tubular vascular graft material made of a layer of expanded polytetrafluoroethelyne (ePTFE) laminated with an ePTFE / elastomer layer and a method of making the same by preforming the graft, longitudinally expanding the graft, sintering the graft, radial expanding the graft using the elastomer matrix to permit radial expansion and compliance of the resulting graft and then wrapping or retreating the outer surface with another layer of the elastomeric material. This patent expressly teaches that standard ePTFE grafts do not hold or resist radial dilatation unless they are wrapped and if wrapped, they are non-compliant. The addition of the elastomer encapsulates the PTFE nodes and fibrils and penetrates into the microporous network of the ePTFE material. Tu, et al. U.S. Pat. No. 5,061,276 issued Oct. 29, 1991 is similar to the '399 Tu, et al. patent but discloses a graft which is made entirely of a PTFE elastomer solution admixture having inner surface distances of 25 microns and outer surface internodal distances of approximately 90 microns. The Tu, et al. U.S. Pat. No. 5,071,609 issued Dec. 10, 1991 discloses a graft made by paste extrusion of a PTFE elastomer admixture, followed by expansion and contraction of the finished product either in the longitudinal or radial direction. This patent teaches that the incorporation of the elastomer is necessary to achieve the property of being expandable and contractible, i.e., compliant in either the radial or longitudinal axis of the graft.

Yamamoto, et al. U.S. Pat. No. 4,830,062 issued May 16, 1989 disclose radial expansion of tetrafluoroethylene tubes to impart porosity in the tube and the resulting heat shrinkability of the radial expanded tetrafluoroethylene tube. This patent does not disclose either the radial expandability of longitudinally expanded ePTFE or the heat shrinkable nature of radial expanded ePTFE.

Interestingly, the Primm U.S. Pat. No. 4,957,669 issued Sep. 18, 1990, discloses a method for radially expanding a tapered ribbed graft, made in accordance with the teachings of Seiler, Jr., et al., U.S. Pat. No. 4,647,416, by mounting the ribbed graft onto an ultrasonic horn having a generally frustroconical tapered shape, restraining the ends, and ultrasonically heating the tubing while stretching the tubing over the tapered shape of the ultrasonic horn. However, this method relies upon ultrasonic heating of the ePTFE material which increases its workability and upon the ultrasonic energy which urges the heated material into the regular tapered frustroconical shape. This method radially expands the PTFE material using the heat and ultrasonic energy as the motive force for expansion. Because the method heats the ePTFE material as it is being urged into conformation with the tapered shape of the ultrasonic horn, the ePTFE microstructure is compromised. Moreover, because of the need for the ultrasonic horn, the conformational shapes which may be formed are limited to simple regular shapes which are capable of easy removal from the ultrasonic horn without compromising the integrity of the ePTFE material.

SUMMARY OF THE INVENTION

The fabrication of irregular-shaped, conformationally complex, medical endoprostheses from biocompatible prosthetic materials, such as ePTFE, has been difficult. Heretofore, those skilled in the art of making endoprostheses suitable for use as vein or arterial grafts, shunts, or the like, have been limited to fashioning the prosthesis of a substantially tubular structure. The surgeon has been left to adapt the tubular structure to the particular application, e.g., end-to-side anastomosis of a distal bypass graft for treating peripheral arterial occlusive disease, such as by fashioning a vein cuff by, for example, making a Miller cuff or a Taylor cuff to minimize compliance mismatch between the synthetic biomaterial and the native arterial tissue. As is reflected in our related patent application, PCT International Application Serial No. PCT/US96/02715, filed Feb. 28, 1996, entitled "Apparatus and Method for Making Flanged End-to-Side Anastomosis," we have discovered a new method of fabricating ePTFE into a flange graft having a tubular body and a flanged end section which is angularly displaced from the longitudinal axis of the graft which entails molding an ePTFE tube by radially expanding a portion of an ePTFE tube into a shaping mold so that the exterior surface of the ePTFE tube is in contact with the shaping mold surface. The present invention offers an alternative approach to forming complex conformations for endoprostheses from ePTFE in which an ePTFE tube is radially expanded to a diameter which is relatively greater than the unexpanded diameter of the ePTFE tube, the radially expanded ePTFE tube is engaged about a shaping mold, then heated which causes the radially expanded ePTFE tube to radially contract about the shaping mold, thereby forming to the external configuration of the shaping mold. Highly constrained regions, or highly tortuous regions may require external wrapping in order to ensure close conformation with the shaping mold. In the inventive method of making an ePTFE endoprosthesis, the shaped ePTFE material has its internal surface in intimate contact with the shaping mold.

DETAILED DESCRIPTION OF THE PREFERRED EMBODIMENTS

The method of the present invention is described in greater detail with reference to the accompanying FIGS. 1–8, in which like features are identified by like reference numerals. The inventive method 10 is set forth in FIG. 1 by its major process steps. PTFE resin 12, preferably a high molecular weight resin such as that sold under the trademark CD 123 (ICI Chemical Company), is blended with an extrusion aid lubricant 14, preferably a mineral spirits solvent, such as that sold under the trademark ISOPAR M (Exxon Chemical Co.). It is preferable that the lubricant be present in an amount between 15–30 wt. % of the PTFE resin, preferably between 18 and 25 wt. %. The weight percent of lubricant to PTFE resin is referred to as the "lubricant level" or "lube level." The admixture of PTFE resin and lubricant is then preformed into an extrusion billet at step 16. The extrusion billet is then extruded in a ram extruder to form tubular extrudates at step 18. The tubular extrudates are then dried at step 20 to evaporate at least a substantial quantity of lubricant present in the extrudate and then longitudinally expanded at step 22. Longitudinal expansion of the dried tubular extrudates imparts the node and fibril microstructure characteristic of ePTFE as taught by U.S. Pat. Nos. 3,953,566, 4,187,390 and 4,482,516, which are hereby expressly incorporated by reference for their teaching of methods of making ePTFE tubes and films. The dried tubular extrudates are then placed into a sintering oven, while restraining the ends against longitudinal shortening, and at least partially sintered.

As used herein, the term "sintered" is intended to refer to the ratio of relative amorphous content of heat treated ePTFE as measured by differential scanning calorimetry wherein the amorphous content is at least 10%. Differential scanning calorimetry is a thermoanalytical method which effectively measures the difference in temperature between the sample and a reference material while both are heated simultaneously by measuring a quantum of additional heat required to maintain the sample and the reference material at a zero temperature differential. A temperature difference signal is generated when there is a $\Delta T$ between the sample and reference. The temperature difference signal is fed into a signal amplifier which drives a separate heater which supplies additional heat equal to the ΔT value. The DSC then measures the heat input in millicalories per second. When the sample reaches a temperature at which an endothermic process, such as a solid-solid transition, e.g., phase change from crystalline to amorphous structure, occurs, the sample will not be heated as rapidly as the reference and a temperature difference appears. Conversely, when a sample reaches a temperature at which an exothermic process occurs, e.g., crystallization, the sample will gain in temperature relative to the reference and a temperature difference will appear. After the onset of each temperature differential, the base line will again approach zero after the process is complete, and subsequent exothermic or endothermic events may be observed as the sample and reference are heated.

As used herein, the terms "partially sintered" or "semi-sintered" are intended to mean that the PTFE material has a crystalline conversion value between about 0.10 and 0.85, preferably 0.20 to 0.75. The crystalline conversion value is calculated using the following equation:

$$\text{Crystalline Conversion} = \frac{\Delta H_1 - \Delta H_3}{\Delta H_1 - \Delta H_2}$$

here $\Delta H_1$ is the heat of fusion of the unsintered PTFE measured by differential scanning calorimetry ("DSC"), $\Delta H_2$ is the heat of fusion of the fully sintered PTFE measured by DSC, and $\Delta H_3$ is the heat of fusion of the semisintered PTFE measured by DSC, where an unsintered PTFE article has a crystalline conversion value of 0 and a fully sintered PTFE article has a crystalline conversion value of 1 and the ePTFE product is dimensionally stable under ambient physiological conditions.

Turning now to FIGS. 2–5 the various equipment used in process 10 are illustrated. A tubular ePTFE member 48, which is at least partially sintered, is co-axially engaged about a dilatation catheter 44 having an inflation balloon 46 carried thereupon. The dilatation catheter 44, inflation balloon 46 and tubular ePTFE member 48 are introduced into a constraining chamber 42. In accordance with the best mode for practicing the invention, the constraining chamber 42 has a generally tubular configuration, having a circular transverse cross-sectional shape, and has an inner diameter which is approximately 200 to 400% greater than the outer diameter of the tubular ePTFE member 48. The constraining chamber 42 is preferably made of any suitable material which is capable of safely withstanding applied radially directed pressures in excess of the burst pressure of the inflation balloon 46. It has been found that a plastic marketed under the trademark LEXAN by DuPont de Nemours is particularly well suited to this application due to its strength and transparency.

Figure 2:
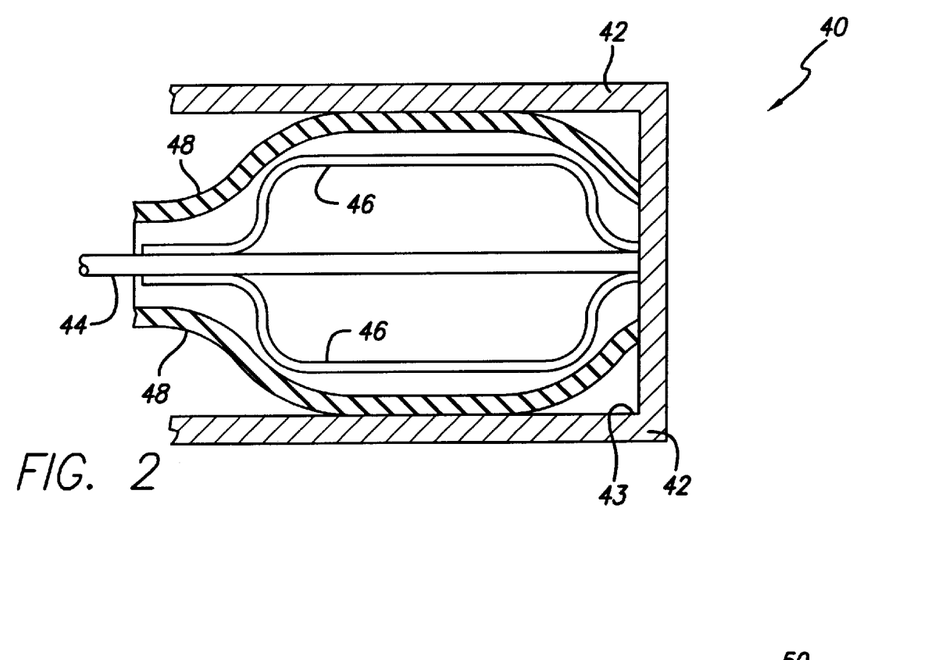
FIG. 2 is a diagrammatic view illustrating the apparatus for radially expanding ePTFE showing a radially expanded ePTFE tube therein.

The tubular ePTFE member 48, inflation balloon 46, and dilatation catheter 44 are introduced into the constraining chamber 42 such that the constraining chamber 42 resides concentrically about the tubular ePTFE member 48. A positive pressure is applied through the dilatation catheter 44 and into the inflation balloon 46 which imparts a radially directed force against the lumenal surface of the tubular ePTFE member. It is known in the art to employ radiopaque saline, Ringers solution or distilled water which is pumped, via a manually or mechanically actuated syringe, through the dilatation catheter 44 and into the inflation balloon 46 as the pressure source. The at least partially sintered tubular ePTFE member 48 will radially expand (step 26) under the influence of the radially outwardly directed fluid pressure being exerted through the inflation balloon 46 until it is in intimate contact with and conforms to the inner surface 43 of the constraining chamber 42. It will be appreciated by those skilled in the art that various configurations of the inner surface 43 of the constraining chamber 42 may be employed to impart a radially expanded shape to the tubular ePTFE member 48. Examples of such alternative dimensional configurations for the constraining chamber 42 include regular shapes such as frustroconical, stepped, or step tapered or irregular shapes, such as bell shaped or horn shaped. Still further, the inner surface 43 of the constraining chamber 42 may have a surface configuration which includes patterns or discontinuities, such as corrugations, recesses or protrusions which will impress a pattern or discontinuity upon the outer surface of the tubular ePTFE member 48 as it is radially expanded into intimate contact with the inner surface 43 of the constraining chamber 42.

Figure 3:
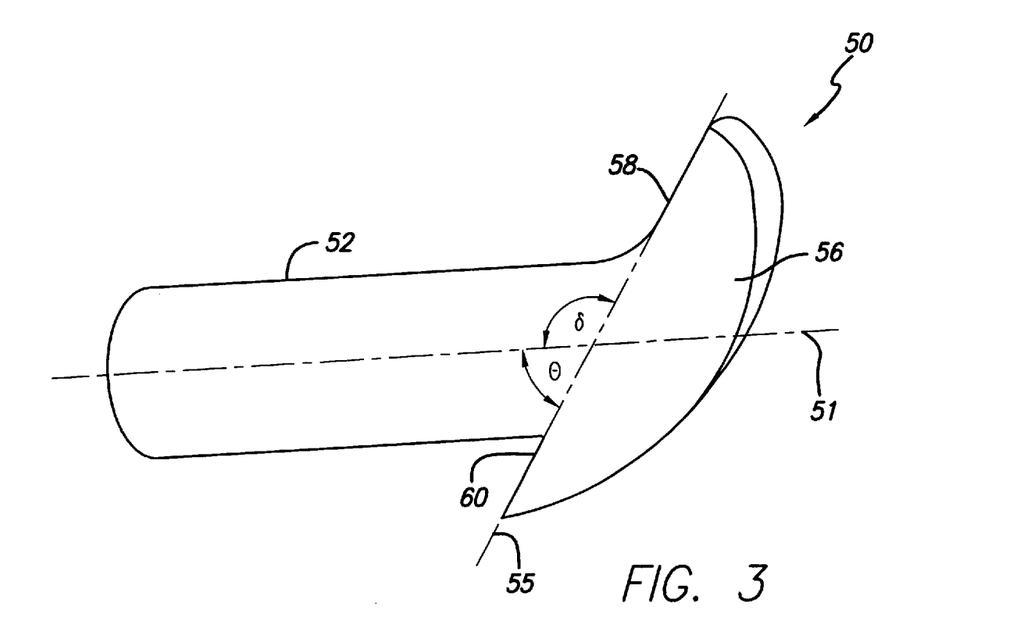
FIG. 3 is a diagrammatic view illustrating a shaping mandrel for shaping rePTFE in accordance with the present invention showing a rePTFE tube engaged thereabout.

A shaping mandrel 50, such as that used to make the inventive flanged graft for end-to-side anastomosis disclosed in co-pending PCT International Application Serial No. PCT/US96/02715, filed Feb. 28, 1996, entitled "Apparatus and Method for Making Flanged End-to-Side Anastomosis," is illustrated in FIG. 3. Shaping mandrel 50 includes a generally cylindrical body section 52 and a radially flared end section 56. To form the flanged graft for end-to-side anastomosis, the radially flared end section 56 has a bell-like shape and is angularly displaced from the longitudinal axis 51 of the shaping mandrel 50. To form the flanged graft for end-to-side anastomosis, the radially flared end section 56 preferably has a toe section 58 which is angularly displaced from the longitudinal axis 51 of the shaping mandrel 50 by an angle δ which is greater than 90° and less than 180° displaced from the longitudinal axis 51 of the shaping mandrel 50. The radially flared end section 56 also preferably has a heel section 60 which is angularly displaced from the longitudinal axis 51 of the shaping mandrel by an angle θ which is less than 90° and greater than 0° displaced from the longitudinal axis 51 of the shaping mandrel 50. The angles δ and θ are measured between the longitudinal axis 51 and a line 55 extending from an outer surface of toe section 58 through the longitudinal axis 51 to the heel section 60.

Figure 4:
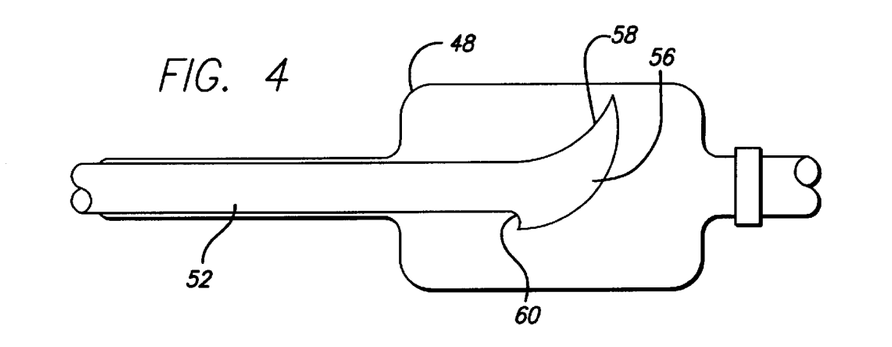
FIG. 4 is a diagrammatic view illustrating engagement of rePTFE about a shaping mandrel.
Figure 5:
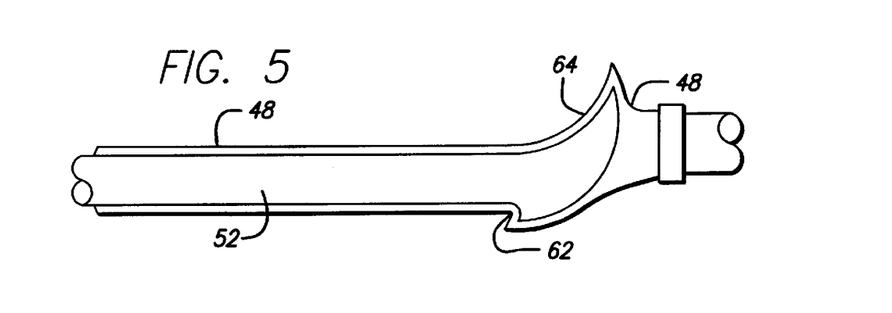
FIG. 5 is a diagrammatic view illustrating engagement of contracted rePTFE about a shaping mandrel.

FIG. 4 depicts engagement of the shaping mandrel 50 concentrically within the radially expanded ePTFE 48 and covering at least a portion of the cylindrical body section 52 and the entire radially flared end section 56, including the toe section 56 and the heel section 60 of the shaping mandrel. Once the ePTFE member 48 is engaged about the shaping mandrel (step 30), the assembly is introduced into a heating oven at a temperature below the second crystalline melt point of the ePTFE member 48 and heated for a period of time sufficient to cause the ePTFE tubular member 48 to radially contract (step 32) about and conform to the shaping member 50 as illustrated in FIG. 5. Depending upon the configuration of the shaping member 50, especially where the flared end section 56 has a heel region 60 having an angle θ which is less than or equal to 45°, to provide an external wrap of polytetrafluoroethylene tape, for example PTFE or TEFLON tape, helically wrapped about the shaping mandrel 50, particularly the flared end section 56 and tensioned thereabout to confine the ePTFE member 48 to the geometry of the flared end section 56.

Figure 6A:
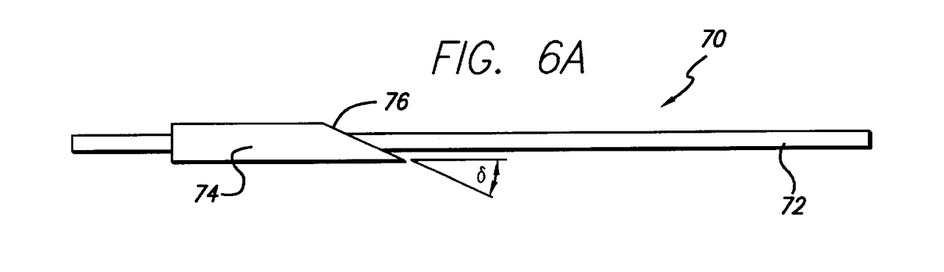
FIG. 6A is a side elevational view of a second embodiment of a shaping mandrel.
Figure 6B:
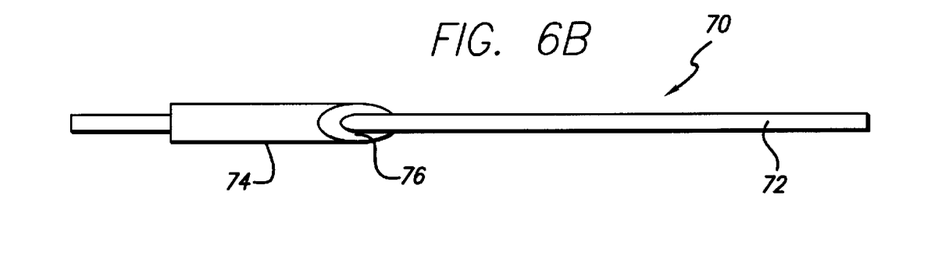
FIG. 6B is a top elevational view of the second embodiment of a shaping mandrel.

FIGS. 6A and 6B depict an alternative embodiment of the shaping mandrel 70 as having an elongate shaft 72 passing along and defining the longitudinal axis of the shaping mandrel 70. The elongate shaft 72 has a transverse cross-sectional diameter which corresponds to the diameter of the non-flared section of the ePTFE end product desired. A generally cylindrical shaping body 74 is provided at a point along the longitudinal axis of the elongate shaft 72 and has a diameter larger than the elongate shaft 72 and corresponding to the desired final diameter of the end product. The cylindrical shaping body 74 has a beveled end section 76 which subtends an angle δ relative to the longitudinal axis of the shaping mandrel 70. Angle δ may assume any desired angular displacement from the longitudinal axis between a value greater than 0 and less than 90, but is preferably between 25° and 45° As with the shaping mandrel 50, it is preferable to make the shaping mandrel 70 of a material which is compatible with ePTFE and is suitable for use in manufacturing implantable medical devices, e.g., stainless steel.

Figure 7:
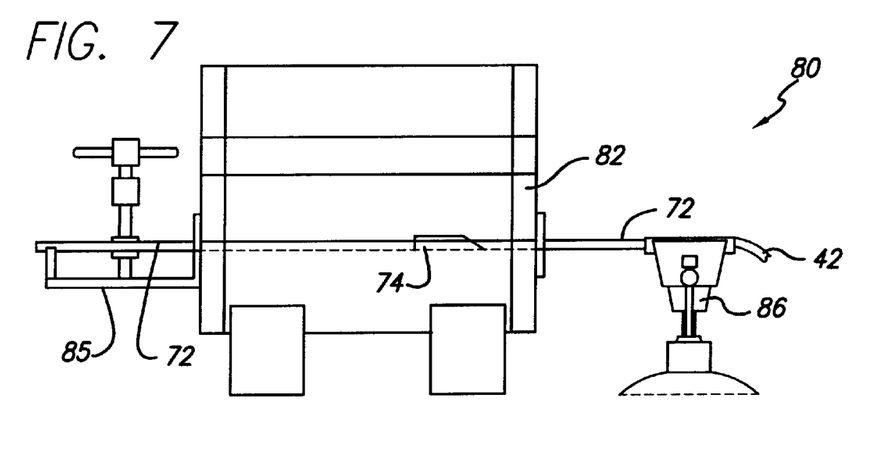
FIG. 7 is a front elevational view of a heating oven assembly and depicting a shaping mandrel and rePTFE engaged thereupon positioned in the heating oven.
Figure 8:
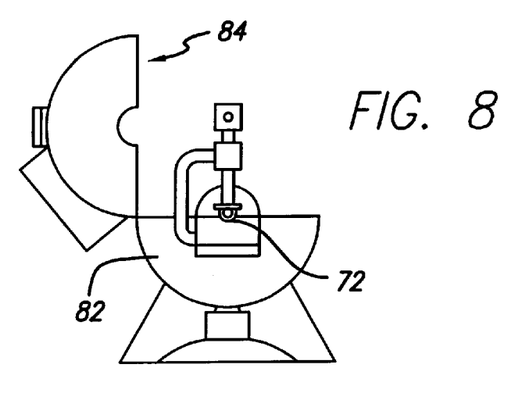
FIG. 8 is an end elevational view of FIG. 7.

FIGS. 7 and 8 depict a heating assembly 80 for inducing radial contraction of the ePTFE member 42 into intimate contact with the configuration of the shaping mandrel 70, specifically the elongate shaft 72 and the cylindrical shaping body 74. The heating assembly consists generally of a clam-shell oven 82 having an electrical induction heating element and ceramic insulation and openings on each opposing lateral end to permit the elongate shaft 72 to pass laterally through the clam-shell oven 82 while exposing the cylindrical shaping body 74 and the portion of the ePTFE member 42 to the heating elements within the clam-shell oven 82. Clamping members 85 and 86 are preferably provided adjacent each opposing lateral end of the clam-shell oven 82 to secure sections of the elongate shaft 72 which project from the clam-shell oven 82.

Figure 1:
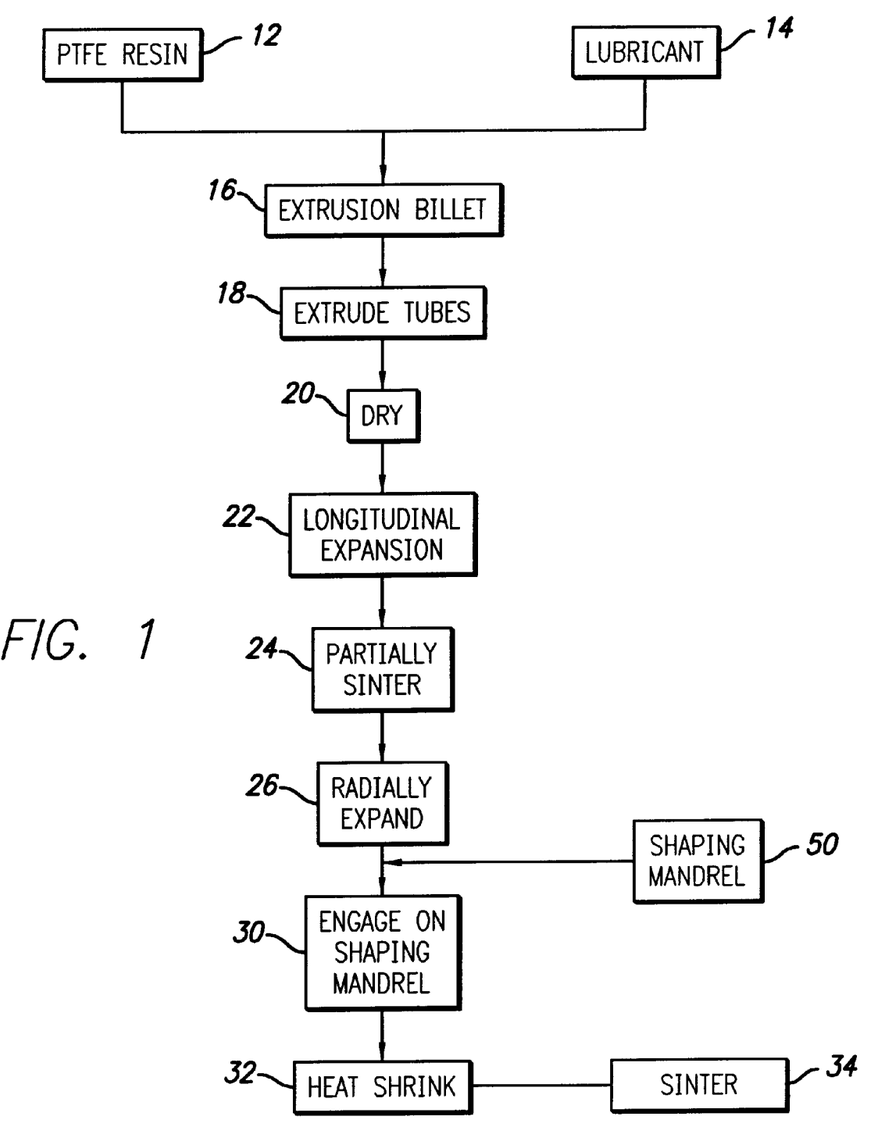
FIG. 1 is a flow diagram of the method for making shaped three-dimensional products from microporous expanded polytetrafluoroethylene in accordance with the present invention.

In accordance with the best mode for practicing the method of the present invention, it is preferable that the step of radially expanding the ePTFE tubular member 26 be carried out at a temperature approximating human body temperature, i.e., be between about 35–45° C. This may be accomplished by radially expanding in heated air or in a heated water bath. Similarly, it preferable that the heat shrink step 32 be performed at a temperature above the first crystalline melt point of PTFE, but below the second crystalline melt point of PTFE, preferably between 327 to 340° C. and that the ePTFE tubular member and the shaping mandrel be subject to heating for between 5 minutes and 10 minutes dwell time in the heating oven, preferably for about 8 minutes. Additionally, prior to heating the ePTFE tubular member during the heat shrink step 32, it is desirable to tightly wrap the ePTFE tubular member about the flared or tapered end section of the shaping mandrel 50, loosely wrap the ePTFE tubular member which is on the elongate shaft of the shaping mandrel and then clamp the ePTFE tubular member sections which project outside the oven to guard against longitudinal contraction during heating.

It will be appreciated that a wide variety of tubular ePTFE articles may be made by the method of the present invention. By altering the three-dimensional conformation of the shaping mandrel, and adding post-processing steps, such as trimming to achieve the final product configuration, the present invention may be adapted to produce a wide variety of tubular medical prosthetic devices.

Figure 9:
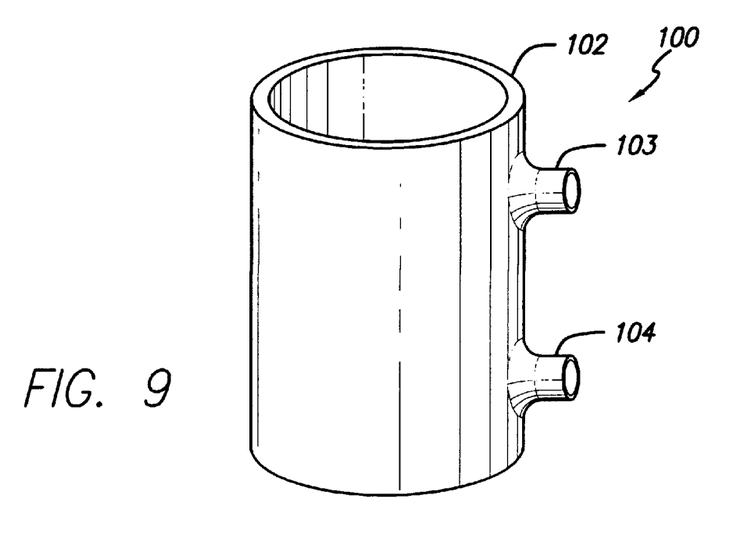
FIG. 9 is a perspective view of an ePTFE tubular member with lateral branches made in accordance with the method of the present invention.

Examples of such other tubular medical prosthetic devices are illustrated in FIGS. 9–12 in the accompanying drawings. Briefly, FIG. 9 depicts a branched vascular graft 100 which consists of an ePTFE tubular body 102 and has a plurality of smaller branch conduits 103 and 104 projecting laterally outward from the tubular body 102. The branch conduits 103 and 104 are positioned about the circumference of the tubular body 102 at a position which is anatomically matched with a patient's corresponding branch conduits. For example, where the ePTFE tubular body 102 is fashioned as an arterial implant in the descending aorta, the plurality of branch conduits 103 and 104 may be positioned to correspond to the anatomic position of the patient's renal arteries to the endogenous renal arteries may be anastomosed to the branch conduits 103 and 104 projecting from the tubular body 102.

Figure 10:
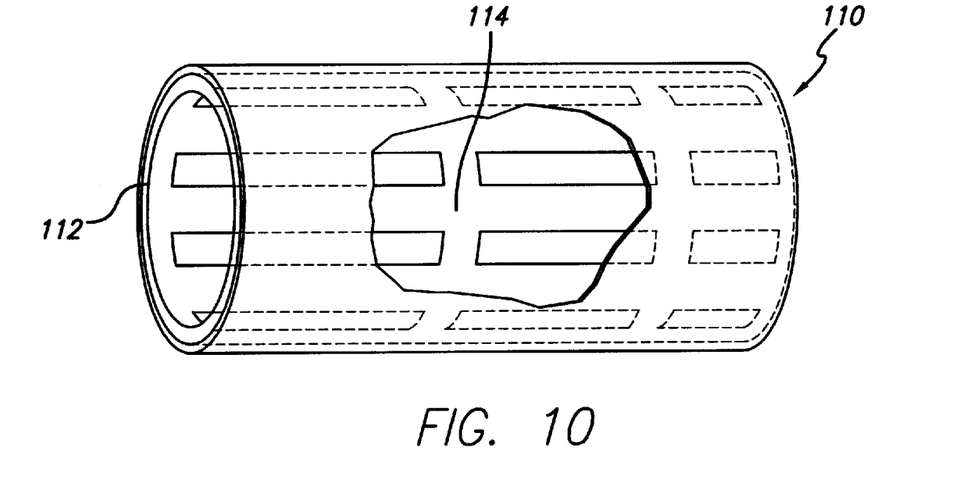
FIG. 10 is a perspective, partial cut-away, view of an endoluminal stent graft made in accordance with the method of the present invention.

FIG. 10 illustrates an endoluminal stent-graft device which is fashioned in accordance with the above-described inventive method, except that an endoluminal stent, such as a PALMAZ stent (Johnson & Johnson Interventional Systems, Inc. Warren, N.J.), a GIANTURCO stent (Cook Medical Corp., Indianapolis, Ind.), a WALLSTENT (Schneider, USA), or a NITINOL stent is substituted from the shaping mandrel and the radially expanded ePTFE tubular member 112 is radially contracted about the stent 114.

Figure 11:
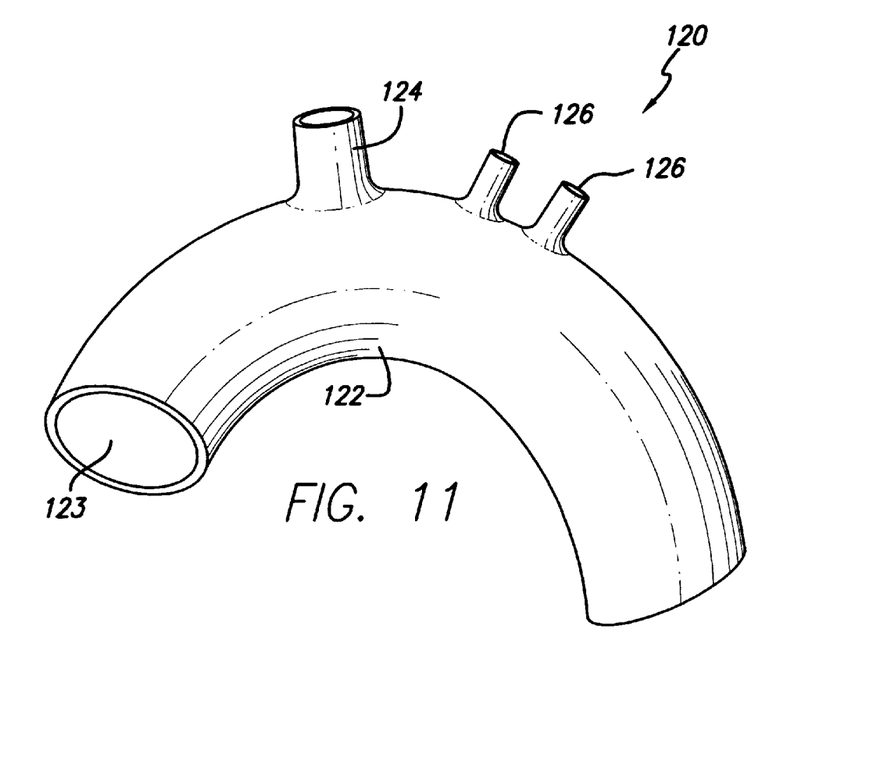
FIG. 11 is a perspective view of a prosthetic aortic arch made in accordance with the method of the present invention.

FIG. 11 illustrates a prosthetic aortic arch 120 consisting of an ePTFE aortic prosthesis 122 having a central lumen 123 and a plurality of branch arterial prosthetic limbs 124, 126 projecting outwardly from the crest of the aortic arch prosthesis 122. The ePTFE aortic prosthesis is fashioned in accordance with the above-described inventive method, except that the shaping mandrel is configured in a C-shape and has a plurality of projections emanating from a position along the length of the shaping mandrel which form the branch arterial prosthetic limbs 124, 126 when the radially expanded ePTFE is radially contracted about the shaping mandrel.

Figure 12A:
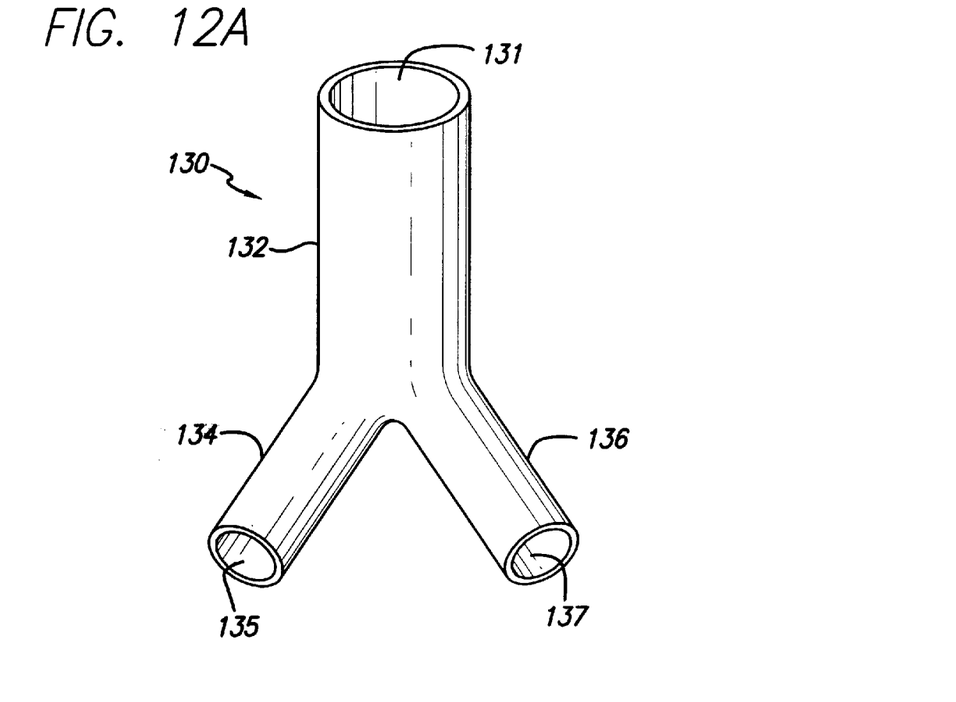
FIG. 12A is a perspective view of a prosthetic bifurcated graft made in accordance with the method of the present invention.

Finally, a bifurcated graft 130, illustrated in FIG. 12A, may be formed in accordance with the above-described inventive method. As with any conventional bifurcated graft prosthesis useful at the femoral branch of the descending aorta, the inventive bifurcated graft 130 consists of a Y-shaped tubular member having a main body portion 132 and a main lumen 131 open to a proximal end of the main body portion 132. The main body portion 132 is bifurcated at a distal end thereof into a plurality of bifurcated tubular members 134, 136, each of the plurality of bifurcated tubular members 134, 136 has an associated bifurcated lumen 135, 137 therein. The bifurcated lumina 135, 137 communicate with the main lumen 131 to conduct a fluid flow, such as blood, through the main lumen 131 and into and through the bifurcated lumina 135, 137. It will be appreciated that the bifurcated graft 130 is not limited to having two bifurcated lumina 135, 137, but may include more than two bifurcations to correspond with a branched anatomical structure having more than two bifurcations.

Figure 12B:
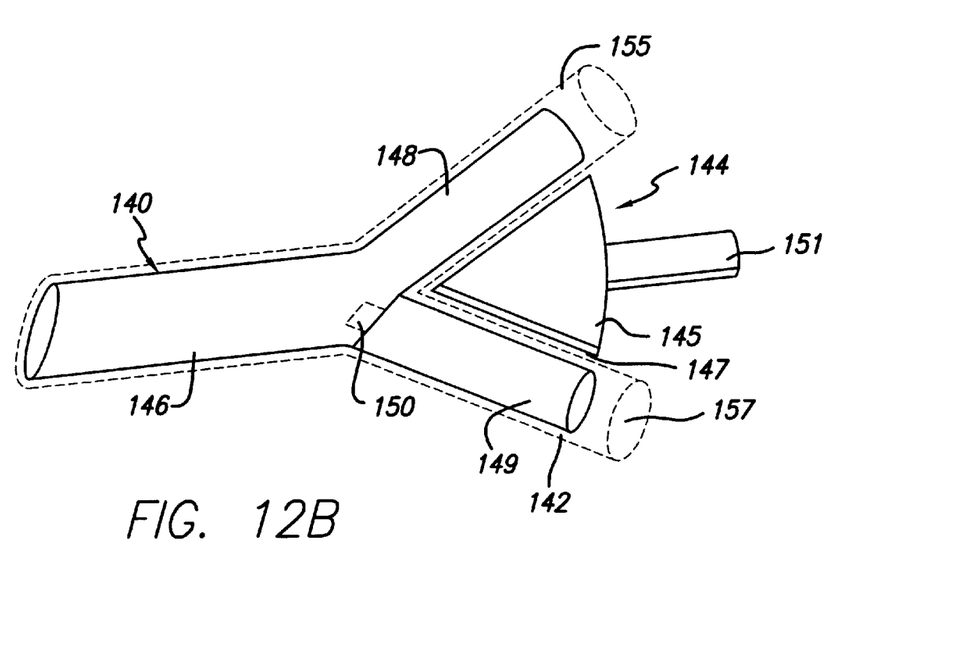
FIG. 12B is a perspective view of a shaping mandrel and crimping member used to make the prosthetic bifurcated graft depicted in FIG. 12A.

The bifurcated graft 130 may be made in accordance with the present invention utilizing the shaping mandrel 140 and crimping member 144 illustrated in FIG. 12B. A partially sintered ePTFE tubular member 142 is radially expanded as described above. A Y-shaped shaping mandrel consisting of a cylindrical main body portion 146 and a plurality of bifurcated leg sections 148, 149 which project from one end of the cylindrical main body portion 146 and are angularly displaced away the longitudinal axis of the shaping member. It is preferable that at least one of the bifurcated leg sections 148, 149 be removably coupled to the cylindrical main body portion 146, such as by a threaded coupling 150, to facilitate removal of the shaping mandrel from the finished bifurcated graft 130.

The radially expanded ePTFE tubular member 142 is engaged concentrically about the Y-shaped shaping mandrel as described above. A crimping member 144, consisting of a pair of generally triangular head members 145, 147 which are co-planar with and superimposable upon one another. A handle member 151 projects outwardly from each of the generally triangular head members 145, 147 and forms a junction at an end opposing the triangular head members 147, 149 (not shown) which permits the crimping member 144 to function in a tong-like or forceps-like manner. It is preferable that either the handle member 151 or the generally triangular head members 145, 147 have a means for applying a positive pressure between the generally triangular head members 147, 149 such that opposing planar surfaces of the generally triangular head members 147, 149 are capable of being brought into intimate contact with one another or into intimate contact with a planar surface interposed between the generally triangular head members 147, 149.

The crimping member 144 is applied over a webbed section of radially expanded ePTFE which subtends the bifurcation of the shaping mandrel 148 and the ePTFE unsupported between the bifurcated leg members 148, 149 is crimped between and in intimate contact with the opposing generally triangular shaped head members 145, 147. A positive pressure is applied to the generally triangular shaped head members 145, 147 to cause the adjacent ePTFE surfaces to come into intimate contact with one another under pressure.

The entire assembly is then heated to a temperature below the second crystalline melt point of PTFE to cause the ePTFE to radially contract over and assume the shape of the shaping mandrel 140. It will be appreciated that by engaging the ePTFE subtending the space between the bifurcated leg members 148, 149, generally tubular leg sections 155, 157 in the ePTFE are formed.

The entire assembly, including the ePTFE 142, the shaping mandrel 140 and the crimping member 144 are then wrapped with PTFE tape to secure the contracted ePTFE onto the shaping mandrel and secure the crimping member 144 in its position relative to the shaping mandrel 140. The wrapped assembly is then introduced into the sintering oven to sinter the ePTFE (step 34). After removal from the sintering oven, the assembly is allowed to cool. The PTFE tape is removed from the assembly, and at least one of the bifurcated leg sections 148, 149 are decoupled from the main body portion 146 of the shaping mandrel and crimping member 144 is removed from the sintered ePTFE shaped graft 142. The sintered ePTFE shaped graft 142 is removed from the shaping mandrel 140 and the ePTFE web subtending the space between the tubular leg sections 155, 157 of the ePTFE graft is trimmed away leaving a seam formed by overlapping and joined sections of the ePTFE tubular member 142.

What is claimed is:

1. A method for shaping expanded polytetrafluorocthylene tubes into a shaped three-dimensional article, comprising the steps of:
    (a) extruding an admixture of polytetrafluoroethylenc resin and lubricant into a tubular extrudate;
    (b) drying the tubular extrudate to remove at least a major fraction of the lubricant;
    (c) longitudinally expanding the tubular extridate forming a longitudinally expanded tubular extrudate with a polytetrafluoroethylene microstructure having a plurality of nodes interconnected by fibrils;
    (d) at least partially sintering the longitudinally expanded tubular extrudate forming an at least partially sintered longitudinally expanded tubular extrudate having a dimensional stability greater than the longitudinally expanded tubular extrudate;
    (e) radially expanding the at least partially sintered tubular extrudate at a temperature greater than ambient but below the crystalline melt point of polytetrafluoroethylene forming a radially expanded at least partially sintered longitudinally expanded tubular extrudate with a diameter greater than that of the at least partially sintered longitudinally expanded tubular extrudate;
    (f) engaging the radially expanded at least partially sintered tubular extrudate circumferentially about a shaping mandrel, the shaping mandrel having a shaped three-dimensional conformation; and
    (g) heating the shaping mandrel and the radially expanded at least partially sintered tubular extrudate, shrinking the radially expanded at least partially sintered tubular extrudate into intimate contact with the shaping mandrel so that said extrudate adopts the three-dimensional conformation of the shaping mandrel.

2. The method according to claim 1, wherein said step of at least partially sintering the longitudinally expanded tubular extrudate results in a crystalline conversion factor of 1 within said extrudate.

3. The method according to claim 1, wherein the step of at least partially sintering the longitudinally expanded tubular extrudate results in a crystalline conversion value between 0.10 and 0.85 within said extrudate.

4. The method according to claim 1, further comprising a step of fully sintering following the step of shrinking the radially expanded at least partially sintered tubular extrudate into intimate contact with the shaping mandrel.

5. The method according to claim 1, wherein the step of heating the shaping mandrel comprises exposing the shaping mandrel and the radially expanded at least partially sintered tubular extrudate to a temperature below the crystalline melt point of polytetrafluoroethylene but above the temperature at which the step of radially expanding the at lest partially sintered tubular extrudate is conducted.

6. A method for shaping expanded polytetrafluoroethylene tubes into a shaped three-dimensional article, comprising the steps of:
    extruding a mixture of polytetrafluorocthylene resin particles and lubricant to form a tubular extrudate;
    drying the tubular extrudate to remove at least a major fraction of the lubricant;
    longitudinally expanding the tubular extrudate to form an expanded polytetrafluoroethylene extridate having a microstructure of a plurality of nodes interconnected by fibrils;
    at least partially sintering the expanded polytetrafluoroethylene extrudate to form a sintered expanded extrudate having a dimensional stability greater than the expanded polytetrafluoroethylene extrudate;
    radially expanding the sintered expanded extrudate at a temperature greater than ambient but below the crystalline melt point of polytetrafluoroethylene forming a radially expanded sintered extrudate with a diameter greater than a diameter of the sintered expanded extrudate;
    engaging the radially expanded sintered extrudate circumferentially about a shaping mandrel, the shaping mandrel having a shaped three-dimensional conformation;
    heating the shaping mandrel and the radially expanded sintered extrudate to shrink the radially expanded sintered extrudate into intimate contact with the shaping mandrel so that said extrudate adopts the three-dimensional conformation of the shaping mandrel; and
    sintering the heat shrunken extrudate.

7. A method for shaping expanded polytetrafluoroethylene tubes into a shaped three-dimensional article, comprising the steps of:

extruding an admixture of polytetrafluoroethylene resin and lubricant into a tubular extrudate;

longitudinally expanding the tubular extrudate forming a longitudinally expanded tubular extrudate with a polytetrafluoroethylene microstructure having a plurality of nodes interconnected by fibrils;

at least partially sintering the longitudinally expanded tubular extrudate forming an at least partially sintered longitudinally expanded tubular extrudate having a dimensional stability greater than the longitudinally expanded tubular extrudate;

radially expanding the at least partially sintered longitudinally expanded tubular extrudate at a temperature greater than ambient but below the crystalline melt point of polytetrafluoroethylene forming a radially expanded at least partially sintered extrudate with a diameter that is 200%–400% greater than that of the at least partially sintered longitudinally expanded tubular extrudate;

engaging the radially expanded at least partially sintered extrudate circumferentially about a shaping mandrel, the shaping mandrel having a shaped three-dimensional conformation; and heating the shaping mandrel and the radially expanded at least partially sintered extrudate, shrinking said extrudate into intimate contact with the shaping mandrel so that said extrudate adopts the three-dimensional conformation of shaping mandrel.

8. The method according to claim 7, wherein said step of at least partially sintering the longitudinally expanded tubular extrudate results in a crystalline conversion factor of 1 within said extrudate.

9. The method according to claim 7, wherein the step of at least partially sintering the longitudinally expanded tubular extrudate results in a crystalline conversion value between 0.10 and 0.85 within said extrudate.

10. The method according to claim 7, further comprising a step of fully sintering following the step of shrinking the radially expanded at least partially sintered tubular extrudate into intimate contact with the shaping mandrel.

11. The method according to claim 7, wherein the step of heating the shaping mandrel comprises exposing the shaping mandrel and the radially expanded at least partially sintered tubular extrudate to a temperature below the crystalline melt point of polytetrafluoroethylene but above the temperature at which the step of radially expanding the at least partially sintered tubular extrudate is conducted.

12. A method for shaping expanded polytetrafluoroethylene tubes into a shaped three-dimensional article, comprising the steps of:

extruding a mixture of polytetrafluoroethylene resin particles and lubricant to form a tubular extrudate;

drying the tubular extrudate to remove a major fraction of the lubricant;

longitudinally expanding the tubular extrudate to form an expanded polytetrafluoroethylene extrudate having a microstructure of a plurality of nodes interconnected by fibrils;

at least partially sintering the expanded polytetrafluoroethylene extrudate to form a sintered expanded extrudate having a dimensional stability greater than the expanded polytetrafluoroethylene extrudate;

radially expanding the sintered expanded extrudate at a temperature greater than ambient but below the crystalline melt point of polytetrafluoroethylene within a constraining chamber to form a radially expanded sintered extrudate with a diameter greater than a diameter of the sintered expanded extrudate, shaped by and in intimate contact with an inner surface of the constraining chamber;

engaging the radially expanded sintered extrudate circumferentially about a shaping mandrel, the shaping mandrel having a shaped three-dimensional conformation;

heating the shaping mandrel and the radially expanded sintered extrudate, shrinking said extrudate so that said extrudate adopts the three-dimensional conformation of the shaping mandrel; and sintering the heat shrunken extrudate.

13. The method according to claim 12, further comprising a step of applying pressure to the radially expanded sintered extrudate to bring said extrudate into intimate contact with the shaping mandrel prior to the heating step.

14. The method according to claim 12, wherein the step of at least partially sintering the expanded polytetrafluoroethylene extrudate results in a crystalline conversion factor of 1 within said extrudate.

15. The method according to claim 12, wherein the step of at least partially sintering the expanded polytetrafluoroethylene extrudate results in a crystalline conversion value between 0.10 and 0.85 within said extrudate.

16. The method according to claim 12, wherein the step of heating the shaping mandrel comprises exposing the shaping mandrel and the radially expanded sintered extrudate to a temperature below the crystalline melt point of polytetrafluoroethylene but above the temperature at which the step of radially expanding the sintered expanded extrudate is conducted.

17. A method for shaping expanded polytetrafluoroethylene tubes into a shaped three-dimensional article, comprising the steps of:

extruding an admixture of polytetrafluoroethylene resin and lubricant into a tubular extrudate;

drying the tubular extrudate to remove at least a major fraction of the lubricant;

longitudinally expanding the tubular extrudate to form an expanded polytetrafluoroethylene extrudate having a microstructure of a plurality of nodes interconnected by fibrils;

at least partially sintering the expanded polytetrafluoroethylene extrudate to form a sintered expanded extrudate having a dimensional stability greater than the longitudinally expanded tubular extrudate;

radially expanding the sintered expanded extrudate at a temperature greater than ambient but below the crystalline melt point of polytetrafluoroethylene to form a radially expanded sintered extrudate with a diameter greater than that of the sintered expanded extrudate;

engaging the radially expanded sintered extrudate circumferentially about a shaping mandrel, the shaping mandrel having a shaped three-dimensional conformation;

applying pressure to the radially expanded sintered extrudate, to bring said extrudate into intimate contact with the shaping mandrel; and heating the shaping mandrel and the radially expanded sintered extrudate, shrinking said extrudate so that said extrudate adopts the three-dimensional conformation of the shaping mandrel.

18. The method according to claim 17, wherein said step of radially expanding takes place within a constraining chamber, wherein the radially expanded sintered extrudate comes into intimate contact with an inner surface of the constraining chamber upon expanding.

19. The method according to claim 17, wherein said step of at least partially sintering the expanded polytetrafluoroethylene extrudate results in a crystalline conversion factor of 1 within said extrudate.

20. The method according to claim 17, wherein the step of at least partially sintering the expanded polytetrafluoroethylene extrudate results in a crystalline conversion value between 0.10 and 0.85 within said extrudate.

21. The method according to claim 17, wherein the step of heating the shaping mandrel comprises exposing the shaping mandrel and the radially expanded sintered extrudate to a temperature below the crystalline melt point of polytetrafluoroethylene but above the temperature at which the step of radially expanding the sintered expanded extrudate is conducted.

* * * * *